United States Patent
Deavenport et al.

(10) Patent No.: US 8,217,201 B2
(45) Date of Patent: Jul. 10, 2012

(54) PROCESS FOR PREPARING QUATERNARY ALKAMMONIUM HALIDES

(75) Inventors: Joseph L. Deavenport, Lake Jackson, TX (US); Rhonda C. Posey, Brazoria, TX (US)

(73) Assignee: Dow Global Technologies LLC, Midland, MI (US)

( * ) Notice: Subject to any disclaimer, the term of this patent is extended or adjusted under 35 U.S.C. 154(b) by 441 days.

(21) Appl. No.: 12/377,488

(22) PCT Filed: Aug. 13, 2007

(86) PCT No.: PCT/US2007/075775
§ 371 (c)(1),
(2), (4) Date: Feb. 26, 2010

(87) PCT Pub. No.: WO2008/022062
PCT Pub. Date: Feb. 21, 2008

(65) Prior Publication Data
US 2010/0160684 A1    Jun. 24, 2010

Related U.S. Application Data

(60) Provisional application No. 60/837,759, filed on Aug. 15, 2006.

(51) Int. Cl.
*C07C 209/60* (2006.01)
*C07C 209/68* (2006.01)

(52) U.S. Cl. ........................ 564/296; 564/476
(58) Field of Classification Search ............... 564/476
See application file for complete search history.

(56) References Cited

U.S. PATENT DOCUMENTS

| 4,054,542 A | 10/1977 | Buckman et al. |
| 4,475,920 A | 10/1984 | Baumann |
| 4,480,126 A * | 10/1984 | Rutzen ............ 564/292 |
| 4,764,306 A * | 8/1988 | Login ............. 554/52 |
| 4,812,263 A * | 3/1989 | Login ............. 562/114 |
| 5,463,127 A | 10/1995 | Deavenport et al. |
| 2005/0194113 A1 | 9/2005 | Lang et al. |

OTHER PUBLICATIONS

Chlebicki et al.; "Preparation, Surface-Actives Properties, and Antimicrobial Activities of Bis-Quartemary Ammonium Salts from Amines and Epichlorohydrin"; Journal of Surfactants and Detergents; Jul. 2005; pp. 227-232; vol. 8; No. 3; AOCS Press.
Kim et al.; "Preparation and Properties of Multiple Ammonium Salts Quaternized by Epichlorohydrin"; Langmuir; 1996; pp. 6304-6308; vol. 12; American Chemical Society.
McKelvey et al.; "Reaction of Epichlorohydrin with Cyclohexylamine"; 1959; pp. 614-616; vol. 24.
Wegrzynska et al.; "Preparation, Surface-Active and Antielectrostatic Properties of Multiple Quaternary Ammonium Salts"; Journal of Surfactants and Detergents; 2006; pp. 221-226; vol. 9; Quarter 3; AOCS Press.

* cited by examiner

*Primary Examiner* — Brian J Davis

(57) ABSTRACT

Alkylammonium halides of the formula are described wherein the alkylammonium halide is prepared by reacting an alkylamine hydrohalide salt and its corresponding free amine with at least two equivalents of an epihalohydrin.

18 Claims, No Drawings

PROCESS FOR PREPARING QUATERNARY ALKAMMONIUM HALIDES

CROSS REFERENCE TO RELATED APPLICATIONS

This application is a 35 USC §371 national phase filing of PCT/US2007/075775 filed Aug. 13, 2007, which claims the benefit of U.S. Provisional Application Ser. No. 60/837,759, filed Aug. 15, 2006.

FIELD

The present invention relates to high purity quaternary alkylammonium halides and methods for preparing the same.

BACKGROUND

Quaternary alkylammonium compounds have a variety of commercial applications, including in the textile industry and the personal care industry. In many of these applications, it is desirable to provide the quaternary alkylammonium compound in a high purity form. Conventional compositions either possess undesirable amounts of impurities or require concentration or purification steps that increase production costs. Consequently, processes for preparing compositions having higher concentrations of the quaternary alkylammonium halide and reduced levels of impurities are much needed and would be very useful.

SUMMARY

The invention provides alkylammonium halides of the formula (I):

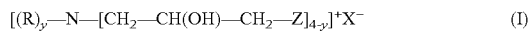

$$[(R)_y-N-[CH_2-CH(OH)-CH_2-Z]_{4-y}]^+ X^- \quad (I)$$

wherein y is 1 or 2; Z is halogen; $X^-$ is halide; and R at each occurrence is independently H or $C_1$-$C_{18}$ alkyl, provided that at least one R is $C_1$-$C_{18}$ alkyl, and wherein the alkylammonium halide is prepared by reacting an alkylamine hydrohalide salt and its corresponding free amine with at least two equivalents of an epihalohydrin.

DETAILED DESCRIPTION

The present invention concerns methods of producing alkylammonium halides of the formula (I):

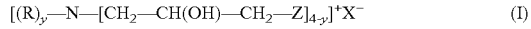

$$[(R)_y-N-[CH_2-CH(OH)-CH_2-Z]_{4-y}]^+ X^- \quad (I)$$

wherein y is 1 or 2, Z is halogen, $X^-$ is halide, and R at each occurrence is independently H or $C_1$-$C_{18}$ alkyl, provided that at least one R is $C_1$-$C_{18}$ alkyl.

The term "alkyl" as used herein is intended to include hydrocarbon-containing groups having 1 to 18 carbon atoms including linear alkyl groups, substituted alkyl groups, branched alkyl groups, and cyclic alkyl groups. Preferred alkyl groups are linear or branched.

Preferred alkylammonium halides of formula (I) include those wherein y is 2.

Preferred alkylammonium halides of formula (I) include those wherein Z is chloro.

Preferred alkylammonium halides of formula (I) include those wherein R is $C_1$-$C_{12}$ alkyl. More preferably, R is $C_1$-$C_6$ alkyl, even more preferably $C_1$-$C_3$ alkyl. A particularly preferred R group is methyl. While the R group at each occurrence may be the same or different, it is preferred that, when more than one R groups are present, all the R groups are the same. While some embodiments include any combination of alkyl groups as the R groups, in particular embodiments each R group (when more than one is present) is the same alkyl group, for example, providing a dimethylammonium-, diethylammonium-, or di-n-propylammonium compound. A preferred quaternary alkylammonium compound is bis(3-chloro-2-hydroxypropyl)dialkylammonium chloride.

Preferred alkylammonium halides of formula (I) include those wherein X is chloride.

An especially preferred alkylammonium halide of formula (I) is bis(3-chloro-2-hydroxypropyl)dimethylammonium chloride.

In one embodiment, the present invention provides methods of making the alkylammonium halide of formula (I) wherein the alkylammonium halide of formula (I) is prepared by reacting an alkylamine hydrohalide salt and its corresponding free amine with at least two equivalents of an epihalohydrin.

It should be understood that the alkylamine is a monoalkylamine or a di-alkylamine. The process is suitable for any mono- or di-alkylamine and the corresponding hydrohalide, such as methylamine, dimethylamine, n-propyl-amine, di-n-propylamine, n-butylamine, di-n-butylamine, n-hexylamine, di-n-hexylamine, and other primary and secondary amines having linear, branched, or cyclic hydrocarbon groups each independently containing from 1 to 18 carbon atoms. More preferably, the process is suitable for dimethylamine and its hydrohalides, particularly its hydrochloride.

The mono- and di-alkylamines and their salts are commercially available, or are formed in reactions within the skill in the art such as the reaction of the corresponding free mono- or di-alkylamine with an acid, preferably a hydrohalic acid, to form the amine hydrohalide salt. Alternatively, one could start with the salt and add free amine (or a strong base to form the free amine from the salt). Any means within the skill in the art for forming mixtures of the free amine and its salt in the preferred pH ranges is suitable.

The pH of the combined alkylamine hydrohalide salt and its corresponding free amine is below about 10, preferably below about 9, and more preferably below about 8. In one embodiment, sufficient amine is admixed with or otherwise present with the amine salt, preferably hydrohalide, to reach an initial pH (before addition of epihalohydrin) of from about 7 to about 10, preferably from 7 to 9, more preferably from 7-8.

In a preferred embodiment, the corresponding free mono- or di-alkylamine is treated with an acid, more preferably with hydrochloric acid to lower the pH and form the salt. While the hydrohalide is preferred, any acid would sufficiently neutralize the base to be useful in the practice of the invention.

In one embodiment, the alkylamine hydrohalide salt and its corresponding free amine are combined before addition of the epihalohydrin to form a pre-mixture. In one embodiment, the pre-mixture is admixed just prior to reaction with epihalohydrin. Alternatively, the pre-mixture is prepared in advance or obtained commercially. If the pre-mixture is stored, it is advantageous to store the pre-mixture in a closed container to prevent free amine from escaping when the amine is volatile.

In a preferred embodiment, the pre-mixture (mono or di-alkylamine and corresponding mono- or di-alkylammonium salt, preferably formed via hydrohalide introduction) is preferably in aqueous solution, most preferably both the amine and hydrohalide are in aqueous solution. In one embodiment, the pre-mixture is substantially free of alcohol solvent. "Substantially free" means concentrations less than 0.1%, preferably less than 0.01%, or more preferably, less than 0.001%.

Any epihalohydrin is suitably used, but epichlorohydrin is the preferred epihalohydrin because it is readily available and chloride ion is considered more environmentally acceptable than other halides. When the amine is a monoalkylamine, at least about two equivalents of epihalohydrin are reacted with the pre-mixture. In particular, two equivalents of epihalohydrin will provide an ammonium halide of formula (I) in which y is 2, and one R is hydrogen. Three or more equivalents of epihalohydrin will provide an ammonium halide of formula (I) in which y is 1 and R is alkyl. When the amine is a dialkylamine, at least about two equivalents of epihalohydrin are reacted with the pre-mixture so that the amine is completely reacted with the epihalohydrin to form the desired product. Preferably, the epihalohydrin to amine plus hydrohalide mole ratio is at least 2.05:1, more preferably about 3:1.

Surprisingly, it has been found that the process, without additional steps, affords compounds with no more than about 20 wt. percent of impurities after extraction. The term "impurities" as used herein means reaction by-products and/or starting materials other than water or solvent. More preferably, no more than about 15 wt. percent of impurities are present. Even more preferably, no more than about 10 wt. percent of impurities are present. Other preferred embodiments have lower concentrations of impurity, such as 7.5 wt. percent, 5 wt. percent, 4 wt. percent, 3 wt. percent, 2 wt. percent, or 1 wt. percent. In one embodiment, the invention provides bis(3-chloro-2-hydroxypropyl)dimethylammonium chloride present in an amount of at least 90 wt. percent. In other embodiments, the bis(3-chloro-2-hydroxypropyl)dimethylammonium chloride is present in an amount of at least 95 wt. percent. In still other embodiments, the bis(3-chloro-2-hydroxypropyl)dimethylammonium chloride is present in an amount of at least 97.5 wt. percent.

Measuring the concentrations of quaternary compounds is within the skill in the art, for instance, by liquid chromatography of an aqueous solution of alkylammonium halide product. Such liquid, preferably paired-ion chromatography is suitably conducted on a system such as the Waters Liquid Chromatograph System commercially available from Millipore, Waters, Chromatography Division. Such a system has a pump, sample injection system, radial column compression system, and a refractive index detector. Suitable columns include, for instance, C-18 reverse-phase columns. A paired-ion chromatography reagent such as that prepared from 3.98 g (grams) of 1-octane sulfonic acid, 143 g sodium perchlorate, 132 g methanol and 1750 g high purity water, filtered through e.g. 0.45 micron paper and degassed 15 minutes under vacuum is suitably used as chromatographic solvent, and a solution such as 5 percent methanol in water (similarly filtered and degassed) is suitably used to flush the column prior to periods of inactivity. These solution concentrations are optionally optimized for some liquid chromatography columns. Determining chromatograph parameters is within the skill in the art, but for the suggested system, suitable combinations include a pump flow rate of 0.8 mL/min. and using a detector having an internal temperature of 40° C. The chromatograph system is preferably used with an integrator, such as that commercially available from Hewlett-Packard and designated as Model 3393. The system is preferably purged with the paired-ion chromatography reagent at least until a flat baseline is obtained. Then a weighed sample is introduced into the system, e.g. using a syringe and sample injection valve. Peaks areas are obtained using the system and an integrator. This procedure is within the skill in the art.

Advantageously, epihalohydrin is added to the pre-mixture. Alternatively, the epihalohydrin, aqueous free amine, and amine hydrohalide are added simultaneously to form the desired product. When the epihalohydrin is added, the temperature is advantageously sufficient to result in a desired reaction rate, conveniently to have the reaction proceed with minimal build-up of reactants and a slow exotherm, but slow enough to avoid appreciable diquaternary compound and dihaloalcohol by-product formation. By appreciable is meant less than 1 weight percent diquaternary compound based upon the weight of the desired product plus diquaternary compound, and less than 10 weight percent dihaloalcohol by-product based upon the weight of the desired product plus dihaloalcohol. The temperature of addition is preferably from about 0° C. to about 25° C., more preferably from about 5° C. to about 20° C., most preferably from about 10° C. to about 15° C.

The epihalohydrin is preferably added to the pre-mixture over a period of time rather than all at once to avoid an exotherm which is difficult to control and leads to high levels of aqueous and organic by-products. Conveniently, it is added over a period of from about 1 to about 4 hours.

Alternatively, the process is continuous and comprises adding the epihalohydrin and pre-mixture in a continuous fashion. The continuous process advantageously has a short residence time in a mixer with a longer residence time in a reactor. A batch process advantageously has the epihalohydrin added slowly to the pre-mixture with continual mixing during and after the addition.

Following addition of the epihalohydrin, the epihalohydrin, amine, and amine hydrohalide mixture are preferably digested for a period of time sufficient to permit the product to form. As used herein, "digest time" refers to the time after addition of epihalohydrin is complete during which additional reaction takes. The digest time is preferably about 1-20 hours at about 10-50° C. More preferably, the reaction is digested for 1-15 hours at about 10° C. and then about 1-3 hours at about 50° C. Even more preferably, the reaction is digested for about 1 hour at about 10° C. and then about 1 hour at about 50° C. Following the digest time, the pH is lowered to about 1 to about 3. Preferably, hydrochloric acid is used to lower the pH and stop the reaction. Some by-products are unavoidably produced and are optionally reacted suitably before, after, or when possible during the process of the invention. For instance, epoxy by-product can optionally be hydrochlorinated with hydrochloric acid.

After the digest time is completed, the epihalohydrin is removed by any means within the skill in the art such as by organic solvent extraction or steam distillation. Other by-products, such as 1,3-dichloro-2-propanol, are also removed. Removal is suitably performed by any method within the skill in the art, but preferably by solvent extraction, such as with methylene chloride. For instance, in a preferred embodiment, the reaction solution is extracted six times with a 2:1 weight ratio of a halogenated solvent, such as methylene chloride. Methylene chloride can then be removed by methods known in the art, such as sparging with nitrogen.

Following removal of the methylene chloride, and without further purification, the product preferably comprises no more than about 20 wt. percent, preferably no more than about 15 wt. percent, even more preferably no more than 10 wt. percent, of impurities.

The following examples are presented to illustrate the invention and are not to be interpreted as limiting it. All percentages, parts and ratios are by weight unless otherwise stated.

EXAMPLES

Example 1

253.24 mL of 40 wt % aqueous dimethylamine (2.00 mol) was added to a 1 L jacketed round bottom flask equipped with a condenser, addition funnel, and pH probe. The pH was decreased to 9 using 195.73 g (1.99 mol) concentrated HCl. 470.34 mL of epichlorohydrin (6.00 mol) was added to the dimethylamine hydrochloride solution over a two hour period at a temperature between 15-20° C. The reaction solution was stirred for an additional 16 hours at 15° C. the solution was extracted with methylene chloride using a 2:1 weight ratio six times to remove the 1,3-dichloro-2-propanol that was generated from the excess epichlorohydrin. The solution was then sparged with nitrogen to remove the residual methylene chloride from the solution. $^{13}$C NMR spectra and HPLC analysis showed the presence of the epoxide form of the desired product. The reaction solution was brought to pH 2 and the temperature increased to 70° C. for one hour to hydrochlorinate the residual epoxide. $^{13}$C NMR spectra and HPLC analysis after the hydrochorination showed very small amounts of the epoxide form. The HPLC chromatograms show a doublet peak for both the chlorohydrin and epoxide forms of the product due to the molecule having two chiral carbon atoms. HPLC analysis showed a purity of 91.7%, with 8.3% impurities.

Example 2

84 mL of 40 wt % aqueous dimethylamine (0.67 mol) was added to a 1 L jacketed round bottom flask equipped with a condenser, addition funnel, and pH probe. The pH was decreased to 7.29 using 63.51 g (0.64 mol) concentrated HCl. 157 mL of epichlorohydrin (2.00 mol) was added to the dimethylamine hydrochloride solution over a 1.25 hour period at a temperature between 10-15° C. The reaction solution was stirred for an additional 1 hour at 15° C. The temperature was increased to 40° C. and maintained for 1.5 hours. The reaction solution was brought to pH 2 using concentrated hydrochloric acid and the temperature increased to 70° C. for one hour. The solution was extracted with methylene chloride using a 2:1 weight ratio seven times to remove the 1,3-dichloro-2-propanol that was generated from the excess epichlorohydrin. The solution was then sparged with nitrogen to remove the residual methylene chloride from the solution. HPLC analysis showed a purity of 97.4%.

Example 3 (Comparative)

8.2 g of dimethylamine hydrochloride were added to 70 mL of ethanol. 20.4 g of epichlorohydrin (2.20:1.00 mole ratio of epi:amine hydrochloride) was slowly added to the dimethylamine hydrochloride/ethanol solution. No free amine was present per this comparative example.

The reaction was allowed to proceed at room temperature for 36 hours whereupon the solvent and residual epichlorohydrin were evaporated from the reaction solution. The resulting viscous liquid was analyzed by 13C NMR and High Performance Liquid Chromatography (procedure described above). The purity of the resulting product was as follows:

TABLE 1

| Compound | % |
| --- | --- |
| Bis(3-chloro-2-hydroxypropyl)dimethylammonium chloride | 59.4% |
| Bis(2,3-epoxypropy)dimethylammonium chloride | 8.7% |
| Bis(2,3-dihydroxypropyl)dimethylammonium chloride | 8.5% |
| 1,3-dichloro-2-propanol | 22.4% |

Using the hydrochloride salt alone under these conditions formed a high amount of dichloropropanol.

In contrast, the present invention includes reacting a mono or di alkylamine hydrohalide salt and its corresponding free amine with at least two equivalents of an epihalohydrin. The combination of mono or di alkylamine hydrohalide salt and its corresponding free amine yields a much purer product, as shown in Examples 1 and 2.

The invention has been described with reference to various specific and preferred embodiments and techniques. However, it should be understood that many variations and modifications may be made while remaining within the spirit and scope of the invention.

The invention claimed is:

1. A process for making an alkylammonium halide of the formula (I):

$$[(R)_y-N-[CH_2-CH(OH)-CH_2-Z]_{4-y}]^+X^- \qquad (I)$$

wherein y is 1 or 2;
Z is halogen;
X— is halide; and
R, at each occurrence, is independently H or $C_1$-$C_{18}$ alkyl, provided that at least one R is $C_1$-$C_{18}$,
the process comprising:
combining a mono or di alkylamine hydrohalide salt and its corresponding free amine to form a pre-mixture; and
reacting said pre-mixture with at least two equivalents of an epihalohydrin.

2. The process of claim 1, further comprising combining the alkylamine hydrohalide salt and its corresponding free amine previous to combination with the epihalohydrin.

3. The process of claim 2, further comprising combining the alkylamine hydrohalide salt and its corresponding free amine in a proportion to achieve a pH less than about 10 in the resulting pre-mixture.

4. The process of claim 2, further comprising combining the alkylamine hydrohalide salt and its corresponding free amine in a proportion to achieve a pH less than about 9 in the resulting pre-mixture.

5. The process of claim 2, further comprising combining the alkylamine hydrohalide salt and its corresponding free amine in a proportion to achieve a pH less than about 8 in the resulting pre-mixture.

6. The process of claim 3, wherein the pre-mixture is substantially free of alcohol solvent.

7. The process of claim 1, wherein y is 2.

8. The process of claim 1, wherein R is unsubstituted C1-C3 alkyl.

9. The process of claim 1, wherein the alkylamine is a dialkylamine.

10. The process of claim 1, wherein the alkylammonium halide of formula (I) is bis(3-chloro-2-hydroxypropyl)dimethylammonium chloride.

11. The process of claim 1, wherein the epihalohydrin is epicholorhydrin.

12. The process of claim 1, wherein the epihalohydrin to amine plus hydrohalide mole ratio is at least 2.05:1.

13. The process of claim 1, wherein the epihalohydrin to amine plus hydrohalide mole ratio is about 3:1.

14. The process of claim 1, further comprising extracting alkylammonium halide of the formula (I) with a halogenated solvent.

15. The process of claim 14, wherein the product of the process comprises no more than about 20 wt. percent of impurities.

16. The process of claim 14, wherein the product of the process comprises no more than about 15 wt. percent of impurities.

17. The process of claim 14, wherein the product of the process comprises no more than about 10 wt. percent, of impurities.

18. The process of claim 14, wherein the product of the process comprises no more than about 4 wt. percent of impurities.

* * * * *